United States Patent [19]

Dolfini et al.

[11] 4,060,630
[45] Nov. 29, 1977

[54] ETHYLENEDIAMINE DERIVATIVES USEFUL IN TREATING SICKLE CELL ANEMIA

[75] Inventors: Joseph E. Dolfini; Robert D. MacKenzie, both of Cincinnati, Ohio

[73] Assignee: Richardson-Merrell Inc., Wilton, Conn.

[21] Appl. No.: 642,782

[22] Filed: Dec. 22, 1975

[51] Int. Cl.$^2$ .............. A61K 31/135; A61K 31/535; A61K 31/495; A61K 31/445
[52] U.S. Cl. ............................ 424/300; 424/248.53; 424/248.56; 424/250; 424/267; 424/274; 424/330; 424/311; 544/165; 260/268 R; 260/293.79; 260/326.47; 260/570 R; 260/570 SC; 560/27
[58] Field of Search ..................... 424/330, 311, 300

[56] References Cited
PUBLICATIONS

*Ann. Soc. Belge Med. Trop.*, (1969), 49, 2, 205–210.

*Primary Examiner*—Frederick E. Waddell
*Attorney, Agent, or Firm*—L. Ruth Hattan; Eugene O. Retter; George W. Rauchfuss, Jr.

[57] ABSTRACT

Compounds of the following general formula are useful in the treatment of sickle cell anemia:

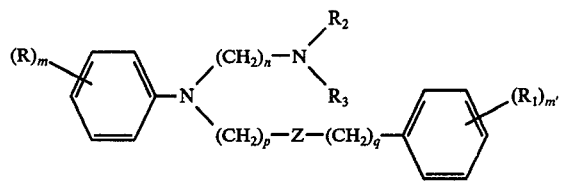

wherein each of R and $R_1$ is hydrogen, chlorine, fluorine, bromine, trifluoromethyl, hydroxy, a lower alkoxy group of from 1 to 4 carbon atoms or a straight or branched lower alkyl group of from 1 to 4 carbon atoms; $R_2$ is hydrogen or a straight or branched lower alkyl group of from 1 to 4 carbon atoms; $R_3$ is hydrogen or a straight or branched lower alkyl group of from 1 to 4 carbon atoms, or when $R_2$ is hydrogen, $R_3$ is $\beta,\beta,\beta$-trichloroethoxycarbonyl, benzyloxycarbonyl, p-methoxybenzyloxycarbonyl, p-nitrobenzyloxycarbonyl or tert-butoxycarbonyl; or $NR_2R_3$ taken together form a monocyclic heterocyclic group selected from the group consisting of pyrrolidino, piperidino, morpholino, and N-(lower)alkylpiperazino; Z is

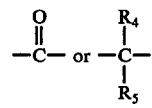

wherein $R_4$ is hydrogen or lower alkyl of from 1 to 4 carbon atoms, and $R_5$ is hydroxy or alkylcarbonyloxy wherein the alkyl moiety has from 1 to 4 carbon atoms; each of $m$ and $m'$ is the integer 1 or 2; $n$ is an integer of from 2 to 6; $p$ is an integer of from 1 to 3; and $q$ is an integer of from zero to 2; or pharmaceutically acceptable acid addition salts and individual optical isomers thereof.

17 Claims, No Drawings phenylacetic, cynnamic, salicylic, and 2-phenoxybenzoic, or, sulfonic acids such as methane sulfonic and 2-hydroxyethane sulfonic acids.

As indicated hereinabove, some of the compounds disclosed herein have been described previously. The compounds of general Formula II are novel. Also, providing that when $R_5$ is hydroxy or alkylcarbonyloxy and the sum of the integers $p$ and $q$ is greater than 1, the compounds of general Formula I are novel. That is, applicants' knowledge, compounds of the following general Formula III represent novel compounds.

Formula III

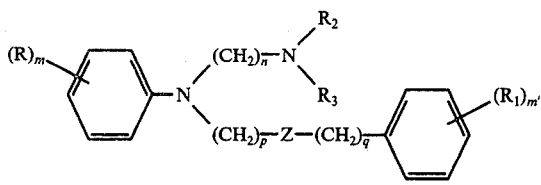

In the above Formula III, each of R and $R_1$ is hydrogen, chlorine, fluorine, bromine, trifluoromethyl, hydroxy, a lower alkoxy group of from 1 to 4 carbon atoms or a straight or branched lower alkyl group of from 1 to 4 carbon atoms; Z is

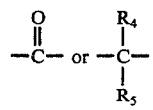

wherein $R_4$ is hydrogen or lower alkyl of from 1 to 4 carbon atoms, and $R_5$ is hydroxy or alkylcarbonyloxy wherein the alkyl moiety has from 1 to 4 carbon atoms; each of $m$ and $m'$ is the integer 1 or 2; $n$ is an integer of from 2 to 6; $p$ is an integer of from 1 to 3; and $q$ is an integer of from zero to 2; $R_2$ is hydrogen and $R_3$ is $\beta,\beta,\beta$-trichloroethoxycarbonyl, benzyloxycarbonyl, p-methoxybenzyloxycarbonyl, p-nitrobenzyloxycarbonyl or tert-butoxycarbonyl; or, each of $R_2$ and $R_3$ is hydrogen or a straight or branched lower alkyl group of from 1 to 4 carbon atoms or each of $R_2$ and $R_3$ taken together with the nitrogen atom to which each is attached form a monocyclic heterocyclic group selected from the group consisting of pyrrolidino, piperidino, morpholino and N-(lower)alkylpiperazino with the proviso that when $R_5$ is hydroxy or alkylcarbonyloxy, the sum of the integers $p$ and $q$ is greater than 1.

It can be seen from the foregoing general Formula I that the compounds described herein are alkylenediamine derivatives wherein one of the nitrogen atoms forms a part of an aniline moiety which nitrogen atom is further substituted with an aralkyl chain containing an oxygen function either as a carbonyl group as represented by the following general Formula IV or a hydroxy group or an alkylcarbonyl derivative thereof as represented by the following general Formula V.

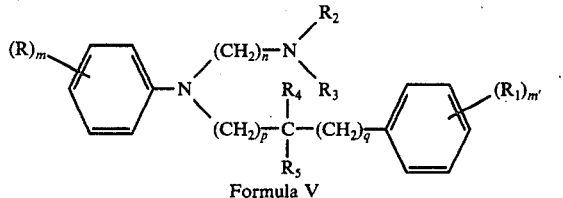

Formula IV

Formula V

In the above general Formulas IV and V the various symbols R, $R_1$, $R_2$, $R_3$, $R_4$, $R_5$, $m$, $m'$, $n$, $p$ and $q$ have the meanings defined in general Formula I. The compounds of general Formula IV represent novel compounds. Also, providing that the sum of the integers $p$ and $q$ is greater than 1, the compounds represented by general Formula V are novel.

Preferred embodiments of this invention include the use of the compound of general Formulas IV and V. Another preferred embodiment of this invention is the use of the compounds of general Formulas IV and V wherein each of $m$ and $m'$ is the integer 1. The use of the compounds of general Formulas IV and V wherein each of $m$ and $m'$ is the integer 2 and each R and $R_1$ substituent is the same is another preferred embodiment of this invention. An additional preferred embodiment of this invention is the use of the compounds of general Formulas IV and V wherein each of $m$ and $m'$ is the integer 2 and each R and $R_1$ substituent is selected from chlorine, fluorine, bromine, hydroxy, a lower alkoxy group of from 1 to 4 carbon atoms and a straight chain alkyl group of from 1 to 4 carbon atoms.

As to the novel compounds described herein as represented by general Formula III preferred embodiments are compounds wherein Z is $$-\underset{R_5}{\overset{R_4}{\underset{|}{\overset{|}{C}}}}-$$

and $R_4$ and $R_5$ have the meanings defined in general Formula III, and compounds wherein Z is a carbonyl moiety. Another preferred embodiment is the novel compounds described herein wherein each of $m$ and $m'$ is the integer 1. The novel compounds described herein wherein each of $m$ and $m'$ is the integer 2 and each R and $R_1$ substituent is the same is another preferred embodiment of this invention. An additional preferred embodiment of this invention is the novel compounds as represented by general Formula III wherein each of $m$ and $m'$ is the integer 2, and each R and $R_1$ substituent is selected from chlorine, fluorine, bromine, hydroxy, a lower alkoxy group of from 1 to 4 carbon atoms and a straight chain alkyl group of from 1 to 4 carbon atoms.

Illustrative examples of the compounds described herein are the following:

N-($\beta$-diethylaminoethyl)-N-($\beta$-hydroxy-$\beta$-phenethyl)-2,5-dichloroaniline N-($\gamma$-diethylaminopropyl)-N-($\beta$-hydroxy-$\beta$-phenethyl)-2,5-dichloroaniline N-($\delta$-diethylaminobutyl)-N-($\beta$-hydroxy-$\beta$-phenethyl)-2,5-dichloroaniline N-($\beta$-ethylaminoethyl)-N-($\beta$-hydroxy-$\beta$-phenethyl)-2,5-dichloroaniline N-($\beta$-aminoethyl)-N-($\beta$-hydroxy-$\beta$-phenethyl)-2,5-dichloroaniline

ETHYLENEDIAMINE DERIVATIVES USEFUL IN TREATING SICKLE CELL ANEMIA

FIELD OF INVENTION

This invention relates to methods of treating sickle cell anemia and novel compounds useful for the same.

BACKGROUND OF THE INVENTION

Compounds of the following structure are described collectively in Great Britain Pat. No. 945,856 and U.S. Pat. No. 3,300,532:

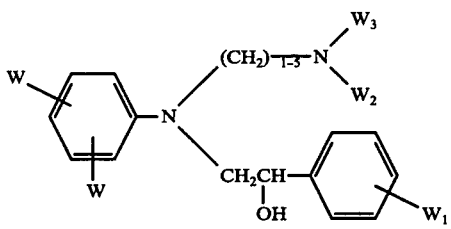

wherein each W represents hydrogen, halogen, or alkoxy; $W_1$ represents hydrogen or alkoxy with the proviso that each of W and $W_1$ may not represent hydrogen at the same time; and $W_2$ and $W_3$ represent alkyl.

Compounds of the above structure wherein the moiety $-(CH_2)-_{1-5}$ is a branched chain are disclosed in Netherlands application No. 7212967 as analgesics. To applicants' knowledge neither the compounds of the above structure nor the compounds of the Netherlands application has been suggested or taught previously for use in treating sickle cell anemia.

SUMMARY OF THE INVENTION

The compounds of the following general Formula I are useful in the treatment of sickle cell anemia.

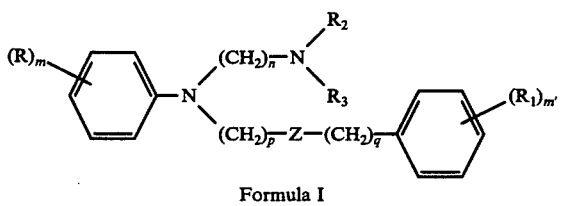

Formula I

In the above Formula I, each of R and $R_1$ is hydrogen, chlorine, fluorine, bromine, trifluoromethyl, hydroxy, a lower alkoxy group of from 1 to 4 carbon atoms or a straight or branched lower alkyl group of from 1 to 4 carbon atoms; $R_2$ is hydrogen or a straight or branched lower alkyl group of from 1 to 4 carbon atoms; $R_3$ is hydrogen or a straight or branched lower alkyl group of from 1 to 4 carbon atoms, or when $R_2$ is hydrogen, $R_3$ is $\beta,\beta,\beta$-trichloroethoxycarbonyl, benzyloxycarbonyl, p-methoxybenzyloxycarbonyl, p-nitrobenzyloxycarbonyl or tert-butoxycarbonyl; or $NR_2R_3$ taken together form a monocyclic heterocyclic group selected from the group consisting of pyrrolidino, piperidino, morpholino and N-(lower)alkylpiperazino; Z is

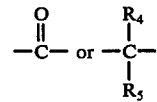

wherein $R_4$ is hydrogen or lower alkyl of from 1 to 4 carbon atoms, and $R_5$ is hydroxy or alkylcarbonyloxy wherein the alkyl moiety has from 1 to 4 carbon atoms; each of m and m' is the integer 1 or 2; n is an integer of from 2 to 6; p is an integer of from 1 to 3; and q is an integer of from zero to 2. The use of the pharmaceutically acceptable acid addition salts and individual optical isomers of the compounds of general Formula I and the pharmaceutically acceptable acid addition salts and individual optical isomers of the novel compounds of general Formula I are also included within the scope of this invention.

DETAILED DESCRIPTION OF INVENTION

Illustrative examples of straight or branched lower alkyl groups of from 1 to 4 carbon atoms which the substituent groups R and $R_1$ may represent are methyl, ethyl, n-propyl, n-butyl, isobutyl, isopropyl, and tert-butyl.

Illustrative examples of lower alkoxy groups of from 1 to 4 carbon atoms which the substituent groups R and $R_1$ may represent methoxy, ethoxy, n-propoxy and n-butoxy.

As used herein, the term alkylcarbonyloxy is taken to mean a moiety as represented by the following:

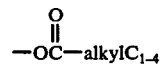

Illustrative examples of alkyl groups of from 1 to 4 carbon atoms present in the alkylcarbonyloxy group are methyl, ethyl, n-propyl and n-butyl.

In the above general Formula I, when the substituent group $R_2$ is hydrogen, the substituent group $R_3$ may be $\beta,\beta,\beta$-trichloroethoxycarbonyl, benzyloxycarbonyl, p-methoxybenzylcarbonyl, p-nitrobenzyloxycarbonyl, or tert-butoxycarbonyl which compounds are depicted by the following general Formula II:

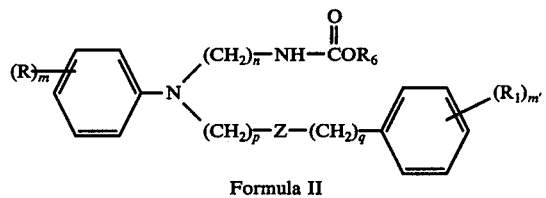

Formula II wherein the various symbols R, $R_1$, m, m', n, p, q, and Z have the meanings defined in general Formula I and $R_6$ is $\beta,\beta,\beta$-trichloroethyl, benzyl, p-methoxybenzyl, p-nitrobenzyl or tert-butyl.

Illustrative examples of pharmaceutically acceptable acid addition salts of the base compounds disclosed herein are those of any suitable inorganic or organic acid. Suitable inorganic acids are for example, hydrochloric, hydrobromic, sulfuric, or phosphoric acids. Suitable organic acids are for example, carboxylic acids such as acetic, propionic, glycolic, lactic, pyruvic, malonic, succinic, fumaric, malic, tartaric, citric, ascorbic, maleic, hydroxy maleic, benzoic, hydroxybenzoic, N-(β-diethylaminoethyl)-N-(β-hydroxy-β-phenyl-propyl)-2,5-dichloroaniline N-(β-diethylaminoethyl)-N-(β-hydroxy-β-phene-thyl)-4-methoxyaniline N-(β-diethylaminoethyl)-N-(β-hydroxy-β-phene-thyl)-4-chloroaniline N-(β-diethylaminoethyl)-N-[β-hydroxy-β-(3,4-dichlorophenethyl)]-2,5-dichloroaniline 1-phenyl-2-[N-(β-diethylaminoethyl)-N-(2,5-dichlorophenyl)amino]ethanol, acetate N-(ε-dimethylaminopentyl)-N-[β-hydroxy-β-(4-ethylphenethyl)]-3-trifluoromethylaniline N-(ω-piperidinohexyl)-N-[γ-hydroxy-γ-(4-methoxyphenylpropyl)]-3,4-di-tert-butylaniline N-(β-pyrrolidinoethyl)-N-[β-hydroxy-γ-(4-ethoxyphenylpropyl)]-4-hydroxyaniline N-(γ-morpholinopropyl)-N-[γ-hydroxy-ε-(4-hydroxyphenylpentyl)]-4-n-butoxyaniline N-[β-(N-methylpiperazino)ethyl]-N-[δ-hydroxy-δ-(3-chlorophenylbutyl)]-4-methylaniline 2-phenyl-3-[N-(β-diethylaminoethyl)-N-(2,5-dichlorophenyl)amino]isopropanol, acetate 1-(4-hydroxyphenyl)-5-[N-(γ-morpholinopropyl)-N-(4-n-butoxyphenyl)amino]-3-pentenol, propionate N-(β-diethylaminoethyl)-N-(β-hydroxy-β-phenylpentyl)-aniline tert-butyl N-[β-[N'-(2,5-dichlorophenyl)-N'-(benzoylethyl)amino]ethyl]carbamate p-nitrobenzyl N-[γ-[N'-(2-bromophenyl)-N'-(phenylmethanol)amino]propyl]carbamate 2-[N-(β-diethylaminoethyl)-N-(2,5-dichlorophenyl)amino]-acetophenone 3-[N-(γ-aminopropyl)-N-(2,5-dichlorophenyl)amino]-4'-methoxypropiophenone 4-[N-(δ-methylaminobutyl)-N-(4-bromophenyl)amino]-4'-bromobutyrophenone 1-[N-(ε-piperidinopentyl)-N-(4-n-propoxyphenyl)amino]-3-phenylpropan-2-one 1-[N-(o-morpholinohexyl)-N-(2,5-dimethylphenyl)amino]-4-phenylbutan-3-one 1-[N-[β-(N-methylpiperazino)ethyl]-N-(phenyl)amino]-5-phenylpentan-4-one 1-[N-(β-di-n-butylaminoethyl)-N-(2,5-difluorophenyl)amino]-4-(4-hydroxyphenyl)butan-2-one 1-[N-(γ-ethylaminopropyl)-N-(4-methoxyphenyl)amino]-5-(4-n-propylphenyl)pentan-3-one 1-[N-(β-diethylaminoethyl)-N-(4-trifluoromethylphenyl)amino]-6-(3,4-dimethoxyphenyl)hexan-4-one.

The compounds disclosed herein including acid addition salts and individual optical isomers are useful in treating sickle cell anemia in a patient in that the compounds are effective in inhibiting the sickling of red blood cells. The utility of the compounds is demonstrated by their ability to prevent in vitro the sickling of red blood cells. Samples of whole blood from patients with sickle cell anemia are subjected to high oxygen tension to reverse any sickled cell to a normal red blood cell shape, after which each sample is divided into control groups and experimental groups. The test compound is added to the experimental group, and each group of whole blood is then subjected to low oxygen tension and at four 15-minute intervals subsequent to the beginning of the test, samples from each group are removed and the number of sickled cells are counted to determine their rate of sickling. The test system is a modification of that described by M. Cawein et al., (in press). The compound N-(β-diethylaminoethyl)-N-(β-hydroxy-β-phenethyl)-2,5-dichloroaniline was found to decrease the rate of sickling for 30 minutes under low oxygen tension at concentrations of 100 and 300 μg/ml. At 60 μg/ml the same compound significantly decreased the rate of sickling for the first 15 minutes of low oxygen tension.

The compounds disclosed herein can be administered alone or in the form of pharmaceutical preparations suitable for oral or parenteral administration. Pharmaceutical compositions containing the novel compounds disclosed herein and conventional pharmaceutical carriers can be employed in unit dosage forms such as solids, for example, tablets and capsules, or liquid solutions, suspensions or elixirs for oral administration, or liquid solutions, suspensions, and emulsions for parenteral use. The quantity of compound administered can vary over a wide range to provide from about 0.01 mg/kg (milligram per kilogram) to about 100 mg/kg of body weight of the patient per day to achieve the desired effect. Unit doses of these compounds can contain from about 50 to 250 mg of the compound and may be administered, for example, from 1 to 4 times daily.

The following are illustrative examples of pharmaceutical preparations.

An illustrative composition for tablets is as follows:

| | | Mg per tablet |
|---|---|---|
| (a) | N-(β-diethylaminoethyl)-N-(β-hydroxy-β-phenethyl)-2,5-dichloroaniline | 100.0 |
| (b) | Wheat starch | 15.0 |
| (c) | Lactose | 33.5 |
| (d) | Magnesium stearate | 1.5 |

A portion of the wheat starch is used to make a granulated starch paste which together with the remainder of the wheat starch and the lactose is granulated, screened and mixed with the active ingredient (a) and the magnesium stearate. The mixture is compressed into tablets weighing 150 mg each.

An illustrative composition for a parenteral injection is the following wherein the quantities are on a weight to volume basis.

| | | Amount |
|---|---|---|
| (a) | N-(β-diethylaminoethyl)-N-(β-hydroxy-β-phenethyl)-2,5-dichloroaniline | 100.0 mg |
| (b) | Sodium chloride | q.s. |
| (c) | Water for injection to make | 20 ml |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

An illustrative composition for hard gelatin capsules is as follows:

| | | Amount mg |
|---|---|---|
| (a) | N-(β-diethylaminoethyl)-N-(β-hydroxy-β-phenethyl)-2,5-dichloroaniline | 200.0 |
| (b) | Talc | 35.0 |

The composition is prepared by passing the dry powders of (a) and (b) through a fine mesh screen and mixing them well. The powder is then filled into No. 0 hard gelatin capsules at a net fill of 235 mg per capsule.

An illustrative composition for pills is the following:

|     |                                                                                | Per pill  |
| --- | ------------------------------------------------------------------------------ | --------- |
| (a) | N-(β-diethylaminoethyl)-N-(β-hydroxy-β-phenethyl)-2,5-dichloroaniline         | 200.0 mg  |
| (b) | Corn starch                                                                    | 130.0 ml  |
| (c) | Liquid glucose                                                                 | 20.0 ml   |

The pills are prepared by blending the active ingredient (a) and the corn starch, then adding the liquid glucose with thorough kneading to form a plactic mass from which the pills are cut and formed.

The ability of the compounds disclosed herein to inhibit the rate of sickling when added in vitro to blood from patients with sickle cell anemia renders the compounds of therapeutic value in controlling the pathophysiological series of events involved in producing morbidity in patients with sickle cell anemia.

The preparations of the following compounds of general Formula I are described in Examples 2, 3, 4, 5 and 6 of U.S. Pat. No. 3,300,532 which synthetic descriptions are incorporated herein by reference thereto.

| Structure | Example No. in U.S. 3,300,532 |
| --- | --- |
| ![CH3O-C6H4-N(CH2CH-C6H5-OH)(CH2)2-N(C2H5)2] | 2, 4 |
| ![2,5-Cl2-C6H3-N(CH2CH-C6H5-OH)(CH2)2-N(C2H5)2] | 3 |
| ![CH3O-C6H4-N(CH2CH(OH)-C6H4-OCH3)(CH2)2-N(C2H5)2] | 5, 6 |

The compounds described herein may be prepared by several means. For example, the compounds may be prepared by reacting an alkylenediamine derivative of the formula

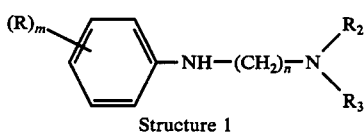

Structure 1 with an alkylating reagent of the formula

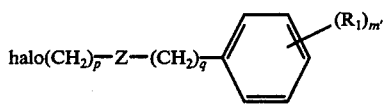

Structure 2 wherein the various substituents, R, $R_1$, $m$, $m'$, $n$, $R_2$, $R_3$, $p$, Z and $q$ have the meanings defined in general Formula I, and halo is a halogen atom. This reaction is best suited for compounds wherein Z is a carbonyl function and $NR_2R_3$ represents a tertiary amine group, that is, each of $R_2$ and $R_3$ is other than hydrogen, or when $R_2$ is hydrogen and $R_3$ is β,β,β-trichloroethoxycarbonyl, benzyloxycarbonyl, p-methoxybenzyloxycarbonyl, p-nitrobenzyloxy, or tert-butoxycarbonyl. This reaction can be carried out in various solvents, for example, alcoholic solvents such as methanol, or ethanol; ethers such as dimethoxythane; in ketone solvents such as methyl isobutyl ketones; in hydrocarbon solvents such as benzene and toluene; and in halogenated hydrocarbons such as chlorobenzene in the presence of an inorganic base such as sodium bicarbonate or potassium bicarbonate or in the presence of an organic base such as triethylamine or an excess of the ethylenediamine reactant. In some cases, it may be desirable to add catalytic amounts of potassium iodide to the reaction mixture. The reaction time is usually about 48 hours, but may vary from about 4 to 120 hours at a temperature of from about 70° C to the reflux temperature of the solvent.

It is more suitable when preparing the compounds described herein wherein both $R_2$ and $R_3$ represent hydrogen, that is, compounds wherein the moiety $NR_2R_3$ represents a primary amine that the ω-nitrogen function be protected with a suitable amine protecting group, such as β,β,β-trichloroethoxycarbonyl, benzyloxycarbonyl, p-methoxybenzyloxycarbonyl, p-nitrobenzyloxycarbonyl or tert-butoxycarbonyl described in more detail hereinafter in the general description and in the specific examples. Upon completion of the above described alkylation reaction, the amine protecting group may be removed by methods known in the art. Thus, the β,β,β-trichloroethoxycarbonyl protecting group can be removed by treating the protected product with 90% aqueous acetic acid and excess zinc metal at 0° C for 2 hours followed by diluting the mixture with water and basifying with sodium hydroxide to pH 10 and extracting the final product with ether. Removal of the benzyloxycarbonyl, p-methoxybenzyloxycarbonyl, p-nitrobenzyloxycarbonyl or p-tert-butoxycarbonyl protecting groups can be achieved by treating the protected product with trifluoroacetic acid at 0° C for 20 to 40 minutes followed by similar work-up.

The compounds described herein wherein the moiety $NR_2R_3$ represents a secondary amine function, that is, compounds wherein one of $R_2$ and $R_3$ is hydrogen and the other such group is a straight or branched lower alkyl group of from 1 to 4 carbon atoms are more appropriately obtained by alkylating the corresponding primary amine compound, that is, a compound wherein each of $R_2$ and $R_3$ is hydrogen with an appropriate alkyl halide wherein the alkyl moiety is straight or branched and has from 1 to 4 carbon atoms, and the halo acid may be chlorine, bromine or iodine. This alkylation reaction is carried out by standard procedures, for example, the reaction conditions described hereinabove for the alkylation reaction between structures 1 and 2 would be suitable.

The compounds described herein wherein Z is

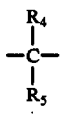

wherein R$_4$ is hydrogen, and R$_5$ is hydroxy can also be prepared by reduction of the corresponding compound wherein Z is carbonyl as illustrated by the following reaction wherein the substituents R, R$_1$, m, m′, R$_2$, R$_3$ n, p and q have the meanings defined in general Formula I.

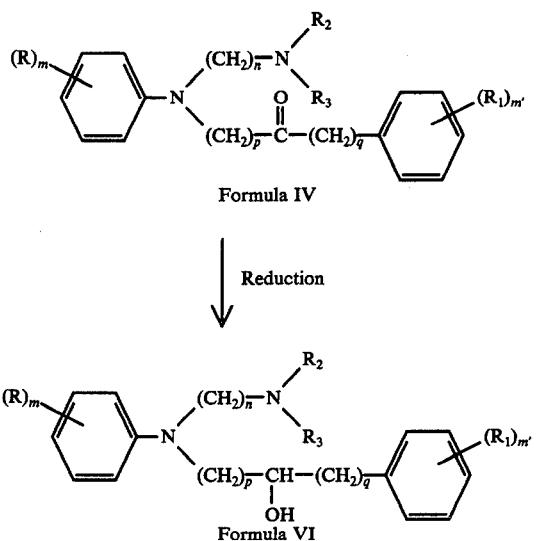

Formula IV

↓ Reduction

Formula VI

Reducing agents such as sodium borohydride may be employed in the above reaction using a lower alcohol solvent such as methanol, isopropyl alcohol and tertiary butanol. The reaction is carried out at temperatures ranging from about 0° C to reflux temperature of the solvent, and the reaction time varies from about 0.5 to about 8 hours. Other hydrides as reducing agents such as lithium aluminum hydride and diborane may also be used in an appropriate solvent such as diethyl ether.

This reduction reaction may also be achieved by catalytic reduction using Raney nickel, palladium, platinum or rodium catalyst in lower alcohol solvents, acetic acid or aqueous mixtures, or by aluminum isopropoxide in isopropanol.

The compounds described herein wherein Z is

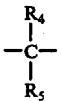

wherein R$_5$ is hydroxy and R$_4$ is lower alkyl of from 1 to 4 carbon atoms are prepared from the corresponding compound wherein Z is carbonyl by a Grignard reaction using a reagent having the formula R$_7$MgX wherein R$_7$ is lower alkyl of from 1 to 4 carbon atoms, and X is a halogen atom. This reaction is carried out under conditions generally known for the addition of Grignard reagents to ketones as described, for example, in J. March, *Advanced Organic Chemistry: Reactions, Mechanisms and Structure*, p. 684, McGraw-Hill Book Co., New York (1968).

Compounds of this invention wherein Z is

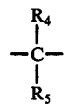

wherein R$_5$ is an alkylcarbonyloxy function are prepared by a standard acylation reaction of the corresponding hydroxy derivative.

As described hereinabove in conjunction with the alkylation reaction of structures 1 and 2 when preparing compounds wherein each of R$_2$ and R$_3$ is hydrogen the ω-nitrogen atom suitably is protected with an appropriate amine protecting group. Similarly, it is desired that when compounds wherein each of R$_2$ and R$_3$ is hydrogen are involved in the above reduction and Grignard reactions that the ω-nitrogen atom be protected with a suitable amine protecting group during the reactions and subsequently removed by the procedures described hereinabove.

Other methods which may be useful in preparing compounds described herein can be found in U.S. Pat. No. 3,300,532.

The alkylenediamine reactants as represented by Structure 1 can be prepared by an alkylation reaction of an appropriately substituted aniline derivative and an ω-haloalkyleneamine derivative as represented by the following wherein the various substituents R, m, n, R$_2$ and R$_3$ have the meanings defined in general Formula I, and halo is a halogen atom such as chlorine or bromine:

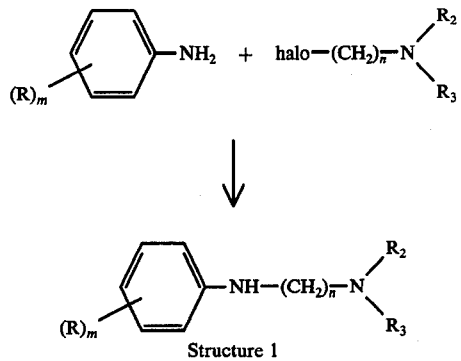

Structure 1

When each of R$_2$ and R$_3$ in the above Structure 1 is hydrogen the nitrogen atom of the ω-haloalkyleneamine starting material is protected by a suitable amine protecting group, such as, β,β,β-trichloroethoxycarbonyl, benzyloxycarbonyl, p-methoxybenzyloxycarbonyl, p-nitrobenzyloxycarbonyl or tert-butoxycarbonyl resulting in compounds of Structure 1 wherein the ω-nitrogen atom carries the protecting group, which compounds can be employed in the aforedescribed alkylation reaction between Structures 1 and 2 when preparing compounds of the invention wherein each of R$_2$ and R$_3$ is hydrogen. The amine protecting group is added to the nitrogen atom of the ω-haloalkylene amine by reacting the latter group with an appropriate formate derivative for example, β,β,β-trichloroethyl chloroformate, benzyl chloroformate, p-methoxybenzyl chloroformate, p-nitrobenzyl chloroformate or tert-butyl azidoformate by procedures generally known in the art and illustrated in detail in the specific examples that follow.

The reaction conditions for the above alkylation reaction are generally the same as described hereinabove for the reaction of compounds as represented by Structures 1 and 2.

The above (R)$_m$— substituted aniline derivatives are known in the art or can be obtained by procedures generally known in the art. Also, some of the aniline derivatives can be used to prepare other aniline derivatives useful in preparing the reactants employed in the preparation of the compounds described herein. For example, the alkoxy substituted aniline derivatives can be prepared by alkylation of the corresponding hydroxy compounds. Alkyl substituted derivatives can be prepared from the corresponding benzene compounds which can be treated with nitric acid in acetic anhydride to give the alkyl substituted nitrobenzene derivatives which can be hydrogenated over palladium to give the alkyl substituted aniline compound. The halogenated and alkoxy substituted benzene derivatives can be similarly treated to give the appropriate aniline compound. The alkoxy substituted nitrobenzene derivatives can also be prepared by treating benzyloxyphenol (CA 73: P 110139s) with an alkylhalide in the presence of a base followed by catalytic hydrogenation with, for example, Pd/H$_2$ and treatment with an appropriate alkylhalide in the presence of a base to give the di-alkoxy substituted benzene which can be nitrated and reduced to the aniline compound as described above. The trifluoromethyl substituted aniline compounds can be prepared by reacting the corresponding benzoic acid derivatives with sulfur tetrafluoride and heating to give the substituted benzene derivative which can be nitrated as described above, or a substituted nitrobenzoic acid derivative can be treated with sulfur tetrafluoride with heating to give the corresponding trifluoromethyl substituted nitro benzene derivative which can be reduced to the corresponding aniline compound. The ω-haloalkyleneamine derivatives are known in the art or can be prepared by an alkylation reaction with an ω-haloalkylene halide wherein the alkylene chain has from 2 to 6 carbon atoms with an amine of the formula NR$_2$R$_3$ wherein R$_2$ and R$_3$ have the meanings defined in general Formula I by the general procedure described hereinabove for an alkylation reaction. The halogen atoms contained on the ω-haloalkylene halide can be chlorine, fluorine, bromine or iodine.

The compounds as represented by Structure 2 are either known in the art or can be prepared by various means. Many of the derivatives wherein Z is carbonyl and q is zero, that is, ω-halo-acetophenone, propiophenone and butyrophenone derivatives are commercially available. Compounds of Structure 2 wherein Z is carbonyl, and p is the integer 1 can be prepared by reacting an acylhalide of the formula

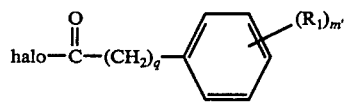

Structure 3 obtained from the corresponding acid by treatment with thionyl chloride by standard procedures, with diazomethane to give the diazoketone derivative (J. March, *Advanced Organic Chemistry: Reactions, Mechanisms and Structure*, p. 370, (1968) McGraw-Hill Book Co., New York) which is subsequently treated with hydrogen bromide or hydrogen chloride to give the respective α-halo ketones. (Ibid., p. 346).

Compounds of Structure 2 wherein Z is carbonyl and p is the integer 2 or 3 are prepared by the addition of an aldehyde of the formula:

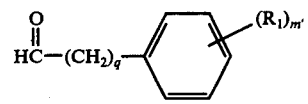

Structure 4 wherein q, R$_1$ and m' have the meanings defined in general Formula I and 1,3-propanedithiol to a solution of boron trifluoride etherate in a refluxing chloroform solution to give a 1,3-dithiane complex as represented by

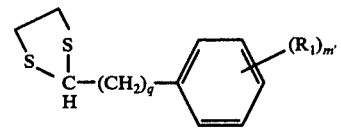

which is converted to the corresponding carbanion salt by treatment with n-butyllithium in tetrahydrofuran under nitrogen atmosphere at about −30° C. The carbanion salt is then alkylated with ω-iodoethylene chloride to give the intermediate

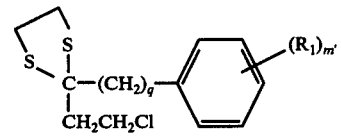

or alkylated with ω-iodopropylenechloride or 1,3-dichloropropane to give the intermediate

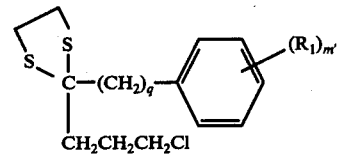

wherein the substituents q, R$_1$ and m' have the meanings defined in general Formula I, each of which is hydrolyzed using mercuric chloride with N-chlorosuccinimide to give the desired reactants by the general procedure described by M. Fieser and L. F. Fieser, *Reactions for Organic Synthesis*, vol. II, pages 182-187, John Wiley and Sons, Inc., New York (1969).

Compounds of Structure 2 wherein Z is carbonyl and p is the integer 2 may also be prepared by a Friedel-Crafts acylation of acyl halide of the formula

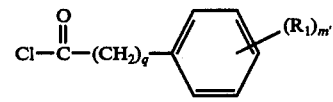

with ethene by procedures generally known in the art.

Compounds of Structure 3, or the acid precursor, and compounds of Structure 4 are known in the art or can be prepared by procedures generally known in the art. The aldehydes as represented by Structure 4 can be oxidized to the corresponding acid which can be converted to the acid halide derivatives as represented by Structure 3, and similarly, the acid halides of Structure 3 can be hydrolyzed to the corresponding aldehydes as represented by Structure 4. Or, the acids used to prepare the acid halides of Structure 3 and the aldehydes as represented by Structure 4 can be prepared by generally known procedures as described, for example, in L. Fieser and M. Fieser, *Organic Chemistry* pages 196–8, 696–698, and pages 195–200, 715–728, D. C. Heath and Co., Boston (1950).

The following examples are further illustrative of the compounds described herein.

EXAMPLE 1

1-Chloro-4-phenyl-butan-3-one

A solution of 0.10 mole of diazomethane in 250 ml of diethyl ether was treated with 0.05 mole of 3-phenylpropionic acid chloride in 50 ml of ether which was added dropwise over a 15 to 30 minute interval at room temperature. After 2 hours the ether solution of the diazo ketone was cooled in an ice bath and dry hydrogen chloride passed into it until nitrogen evolution ceased. The ethereal solution was then washed with ice water and a 5% aqueous sodium carbonate solution. The organic layer was dried over anhydrous sodium sulfate, filtered, and evaporated to dryness leaving an oil.

EXAMPLE 2

1-Chloro-5-phenylpentan-3-one

A solution of 0.10 mole of 3-phenylpropionaldehyde in 0.11 mole of 1,3,-propandithiol and 2 ml of boron-trifluoride etherate in 200 ml of chloroform was refluxed for 1 hour. The reaction mixture was washed with 50 ml of cold water and 50 ml of 5% aqueous sodium carbonate. The organic layer was dried over sodium sulfate, filtered and evaporated to give a 1,3-dithiane complex. A solution of 0.10 mole of the 1,3-dithiane complex in 100 ml of dry tetrahydrafuran was chilled at −15° C under an argon atmosphere. Into the chilled solution was syringed an equivalent amount of n-butyllithium hexane. The mixture is stirred for 15 minutes after which 0.10 mole of 1-chloro-2-iodoethane in 50 ml of tetrahydrofuran was rapidly added maintaining the temperature below 15° C. Upon completion of the addition stirring was continued for 1 hour after which the solution was allowed to warm to room temperature then poured into 200 ml of cold aqueous sodium carbonate and extracted with diethyl ether. The organic extract was washed with saturated aqueous sodium chloride, dried over sodium sulfate, filtered and evaporated in vacuo to give the alkylated 1,3-dithiolane intermediate.

A solution of 0.05 mole of the alkylated 1,3-dithiolane intermediate was dissolved in 50 ml of acetone-water (3:2). To the solution was added 0.10 mole of cadmium chloride, and the resulting mixture stirred vigorously while 0.10 mole of mercuric chloride was added at room temperature. After 24 hours, the reaction mixture was filtered and poured into ice water. The resulting suspension was extracted with ether and the organic extract was washed with brine, dried over sodium sulfate, filtered and the solvent evaporated in vacuo to give 1-chloro-5-phenylpentan-3-one.

EXAMPLE 3

6-Chloro-1-phenylhexan-3-one

When in the procedure of Example 2 0.10 mole of 1-chloro-3-iodopropane is substituted for 1-chloro-2-iodoethane, 6-chloro-1-phenylhexan-3-one is obtained.

EXAMPLE 4

5-Chloro-1-phenylpentan-2-one

When in the procedure of Example 2 0.10 mole of phenylacetaldehyde is substituted for 3-phenylpropionaldehyde, and 0.10 mole of 1-chloro-3-iodopropane is substituted for 1-chloro-2-iodoethane, 5-chloro-1-phenylpentan-2-one is obtained.

EXAMPLE 5

2-[N-(2,5-dichlorophenyl)-N-($\beta$-diethylaminoethyl)amino]-acetophenone

A solution of 0.05 mole of N-(2,5-dichlorophenyl)-N',N'-diethylethylenediamine obtained by alkylating 2,5-dichloroaniline with N,N-diethyl-$\beta$-chloroethylamine, and 0.05 mole of 2-chloroacetophenone in dimethoxyethane containing 0.05 mole of triethylamine was stirred at room temperature for 24 hours under a nitrogen atmosphere after which the solvent was removed at reduced pressure. The residue was dissolved in 200 ml of chloroform and washed with 5% aqueous sodium carbonate, dried over sodium sulfate and evaporated to dryness to give 2-[N-(2,5-dichlorophenyl)-N-($\beta$-diethylaminoethyl)amino]acetophenone.

When in the procedure of Example 5 an appropriate amount of an amine listed in the following Table I is reacted with an appropriate amount of a ketone derivative listed in the following Table I the respective products listed in Table I are obtained.

TABLE I

| AMINE REACTANT | KETONE REACTANT | KETONE PRODUCT |
| --- | --- | --- |
| N,N-dimethyl-N'-phenyl-ethylenediamine | 1-chloro-4-phenylbutan-2-one | 1-[N($\beta$-dimethylaminoethyl)-N-phenylamino]-4-phenylbutan-2-one |
| N,N-dimethyl-N'-phenyl-ethylenediamine | 1-chloro-5-phenylpentan-3-one | 1-[N-($\beta$-dimethylaminoethyl)-N-phenylamino]-5-phenylpentan-3-one |
| N,N-dimethyl-N'-phenyl-ethylenediamine | 6-chloro-1-phenylhexan-3-one | 6-[N-($\beta$-dimethylaminoethyl)-N-phenylamino]-1-phenylhexan-3-one |
| N,N-dimethyl-N'-phenyl-ethylenediamine | 5-chloro-1-phenylpentan-2-one | 5-[N-($\beta$-dimethylaminoethyl)-N-phenylamino]-1-phenylpentan-2-one |
| N,N-dimethyl-N'-phenyl-ethylenediamine | 4-chlorobutyrophenone | 4-[N-($\beta$-dimethylaminoethyl)-N-phenylamino]-butyrophenone |
| N,N-diethyl-N'-phenyl-ethylenediamine | 1-chloro-4-phenylbutan-2-one | 1-[N-($\beta$-diethylaminoethyl)-N-phenylamino]-4-phenylbutan-2-one |
| N,N-dimethyl-N'-phenyl-propylenediamine | 1-chloro-5-phenylpentan-3-one | 1-[N-($\gamma$-dimethylaminopropyl)-N-phenylamino]-5-phenylpentan-3-one |
| N-(4-chlorophenyl)-N'-ethyl-N'-methylpropyl-enediamine | 1-chloro-5-(4-chlorophenyl)-pentan-3-one | 1-[N-(4-chlorophenyl)-N-[$\gamma$(N'-ethyl-N'-methylamino])propyl]amino]-5-(4-chlorophenyl)pentan-3-one |
| N-(2,5-dichlorophenyl)-N',N'-diethylpropylene- | 2-chloroacetophenone | 2-[N-(2,5-dichlorophenyl)-N-($\gamma$-diethylaminopropyl)amino]acetophenone |

TABLE I-continued

| AMINE REACTANT | KETONE REACTANT | KETONE PRODUCT |
|---|---|---|
| diamine | | |
| N-(2,5-dichlorophenyl)-N',N'-diethylbutylene-diamine | 2-chloroacetophenone | 2-[N-(2,5-dichlorophenyl)-N-(δ-diethyl-aminobutyl)amino]acetophenone |
| N,N-di-n-propyl-N'-(4-methoxyphenyl)pentylene-diamine | 2-chloro-2',5'-dichloroaceto-phenone | 2',5'-dichloro-2-[N-(ε-di-n-propylamino-pentyl)-N-(4-methoxyphenyl)amino]aceto-phenone |
| N,N-di-n-butyl-N'-(2,5-dimethoxyphenyl)ethylene-diamine | 2-chloroacetophenone | 2-[N-(β-di-n-butylaminoethyl)-N-(2,5-di-methoxyphenyl)amino)amino]acetophenone |
| N-(3-piperidinopropyl)-3-n-propylaniline | 1-chloro-4-(3,4-diethoxyphenyl)-butan-2-one | 1-[N-(γ-piperidinopropyl)-N-(3-n-propyl-phenyl)amino]-4-(3,4-diethoxyphenyl)butan-2-one |
| 4-hydroxy-N-(2-morpholino-ethyl)aniline | 3-chloro-4'-hydroxypropiophenone | 4'-hydroxy-3-[N-(β-morpholinoethyl)-N-(4-hydroxyphenylamino]propiophenone |
| N-(2-pyrrolidinoethyl)-aniline | 4'-n-butyl-3-chloropropiophenone | 4'-n-butyl-3-[N-(β-pyrrolidinoethyl)-N-phenylamino]propiophenone |

EXAMPLE 6

2-[N-(β-Aminoethyl)-N-(2,5-dichlorophenyl)amino]-acetophenone

A. One mole of 1-amino-2-chloroethane hydrochloride in 500 ml of dimethylformamide at 0° C is treated with 1 mole of β,β,β-trichloroethyl chloroformate after which a solution of 2 moles of triethylamine in 200 ml of dimethylformamide is slowly added. Upon completion of the addition, the reaction is diluted with 2 liters of water and extracted twice with 750 ml of ether. The ether extracts are washed twice with 500 ml of water then twice with 500 ml of 1 M HCl, dried over sodium sulfate and evaporated to dryness to give β,β,β-trichloroethyl N-(2-chloroethyl)carbamate.

B. A mixture of 0.1 mole of β,β,β-trichloroethyl N-(2-chloroethyl)carbamate and 0.1 mole of 2,5-dichloroaniline in 500 ml of isopropyl alcohol containing 0.1 mole of potassium carbonate is stirred for 5 hours at 25° C after which the reaction mixture is diluted with 1.5 liters of water and extracted twice with 300 ml of ether. The ether extracts are washed with saturated aqueous sodium bicarbonate, dried over sodium sulfate and evaporated to dryness to give β,β,β-trichloroethyl N-[β-(2,5-dichloroaniline)ethyl]carbamate.

C. When in the procedure of Example 5 an appropriate amount of β,β,β-trichloroethyl N-[β-(2,5-dichloroaniline)ethyl]carbamate is substituted for N-(2,5-dichlorophenyl)-N',N'-diethylethylenediamine, β,β,β-trichloroethyl N-[β-[N'-(2,5-dichlorophenyl)-N'-(benzoylmethyl)amino]ethyl]carbamate is obtained. The β,β,β-trichloroethoxycarbonyl protecting group is removed from the amino nitrogen by treating the amine protected compounds with 90% aqueous acetic acid and excess zinc metal at 0° C for 2 hours followed by diluting the mixture with water, adjusting the pH to 10 using sodium hydroxide and extracting with ether to give 2-[N-(β-aminoethyl)-N-(2,5-dichlorophenyl-)amino]acetophenone.

When in the above procedure 6 (B) an appropriate amount of p-trifluoromethylaniline is substituted for 2,5-dichloroaniline β,β,β-trichloroethyl N-[β-(4-trifluoromethylaniline)ethyl]carbamate is obtained which can be substituted for β,β,β-trichloroethyl N-[β-(2,5-dichloroaniline)ethyl]carbamate in the above procedure 6 (C) to give 2-[N-(β-aminoethyl)-N-(4-trifluoromethylphenyl)amino]acetophenone.

EXAMPLE 7

N-(β-Diethylaminoethyl)-N-(β-hydroxy-β-phenethyl)-2,5-dichloroaniline

A solution of 0.05 mole of 2-[N-(2,5-dichlorophenyl)-N-(β-diethylaminoethyl)amino]acetophenone in 150 ml of ethylacetate is catalytically hydrogenated using 1 gram of platinum oxide at 40–50 psi until one equivalent of hydrogen is taken up. The catalyst is filtered off and the solvent is evaporated in vacuo yielding N-[β-hydroxy-β-phenethyl]-2,5-dichloroaniline.

When in the procedure of Example 7 an appropriate amount of a ketone product listed in the above Table I is substituted for 2-[N-(β-aminoethyl)-N-(2,5-dichlorophenyl)amino]acetophenone the following respective products are obtained.

N-(β-dimethylaminoethyl)-N-(β-hydroxy-δ-phenyl-butyl)aniline
N-(β-dimethylaminoethyl)-N-(γ-hydroxy-ε-phenyl-pentyl)aniline
N-(β-dimethylaminoethyl)-N-(δ-hydroxy-ω-phenyl-hexyl)aniline
N-(β-dimethylaminoethyl)-N-(δ-hydroxy-ε-phenyl-pentyl)aniline
N-(β-dimethylaminoethyl)-N-(δ-hydroxy-δ-phenyl-butyl)aniline
N-(β-diethylaminoethyl)-N-(β-hydroxy-δ-phenyl-butyl)aniline
N-(γ-dimethylaminopropyl)-N-(γ-hydroxy-ε-phenyl-pentyl)aniline
N-[γ-(N'-ethyl-N'-methylamino)propyl]-N-[γ-hydroxy-ε-(4-chlorophenyl)pentyl]-4-chloroaniline
N-(γ-diethylaminopropyl)-N-(β-hydroxy-β-phene-thyl)-2,5-dichloroaniline
N-(δ-diethylaminobutyl)-N-(β-hydroxy-β-phene-thyl)-2,5-dichloroaniline
N-(β-diethylaminoethyl)-N-(β-hydroxy-β-phene-thyl)-2,5-dichloroaniline
N-(ε-di-n-propylaminophenyl)-N-[β-hydroxy-β-(2,5-dichlorophenyl)ethyl]-4-methoxyaniline
N-(β-di-n-butylaminoethyl)-N-(β-hydroxy-β-phene-thyl)-2,5-dimethoxyaniline
N-(γ-piperidinopropyl)-N-[β-hydroxy-δ-(3,4-diethoxyphenyl)butyl]-3-n-propylaniline
N-(β-morpholinoethyl)-N-[γ-hydroxy-γ-(4-hydroxyphenyl)propyl]-4-hydroxyaniline
N-(β-pyrrolidinoethyl)-N-[γ-hydroxy-α-(4-n-butylphenyl)propyl]aniline

EXAMPLE 8

N-(β-diethylaminoethyl)-N-(β-hydroxy-β-phenyl-propyl)-2,5-dichloroaniline

A solution of 0.10 mole of 2-[N-(2,5-dichlorophenyl)-N-(β-diethylaminoethyl)amino]acetophenone in 200 ml of dry diethylether is added to a solution of 0.10 mole of methylmagnesium iodide in 500 ml of dry diethylether maintained at a temperature of from 0° to −5° C under nitrogen atmosphere. Thirty minutes after the addition the reaction mixture is washed with ice cold aqueous 2M ammonium chloride, dried over sodium sulfate, filtered and evaporated to give N-(β-diethylaminoethyl)-N-(β-hydroxy-β-phenylpropyl)-2,5-dichloroaniline.

In a similar manner, by reaction of an appropriate ketone as described by general Formula IV with an alkyl Grignard reagent wherein the alkyl moiety contains from 1 to 4 carbon atoms other compounds described herein as represented by general Formula V wherein $R_4$ is lower alkyl may be obtained.

EXAMPLE 9

N-(β-Aminoethyl)-N-(β-hydroxy-β-phenethyl)-2,5-dichloroaniline

When in the procedure of Example 7 an appropriate amount of β,β,β-trichloroethyl N-[β-[N'-(2,5-dichlorophenyl)-N'-(benzoylmethyl)amino]ethyl]carbamate is substituted for 2-[N-(2,5-dichlorophenyl)-N-(β-diethylaminoethyl)amino]acetophenone, β,β,β-trichloroethyl N-[β-[N'-(2,5-dichlorophenyl)-N'-(β-hydroxy-β-phenethyl)amino]ethyl]carbamate is obtained and treated with 90% aqueous acetic acid and excess zinc metal at 0° C for 2 hours after which the mixture is diluted with water, basified with sodium hydroxide to pH 10 and extracted with ether to give N-(β-aminoethyl)-N-(β-hydroxy-β-phenethyl)-2,5-dichloroaniline.

EXAMPLE 10

N-(β-Aminoethyl)-N-(β-hydroxy-β-phenylpropyl)-2,5-dichloroaniline

When in the procedure of Example 8 an appropriate amount of β,β,β-trichloroethyl N-[β-[N'-(2,5-dichlorophenyl)-N'-(benzoylmethyl)amino]ethyl]carbamate is substituted for 2-[N-(2,5-dichlorophenyl)-N-(β-diethylaminoethyl)amino]acetophenone, β,β,β-trichloroethyl N-[β-[N'-(2,5-dichlorophenyl)-N'-(β-hydroxy-β-phenylpropyl)amino]ethyl]carbamate is obtained and treated with 90% aqueous acetic acid and excess zinc metal at 0° C for 2 hours after which the mixture is diluted with water, basified with sodium hydroxide to pH 10 and extracted with ether to give N-(β-aminoethyl)-N-(β-hydroxy-β-phenylpropyl)-2,5-dichloroaniline.

EXAMPLE 11

2-[N-(β-Ethylaminoethyl)-N-(2,5-dichlorophenyl)amino]acetophenone

When in the procedure of Example 5 an appropriate amount of 2-[N-(β-aminoethyl)-N-(2,5-dichlorophenyl)amino]acetophenone is substituted for N-(2,5-dichlorophenyl)-N',N'-diethylethylenediamine and an appropriate amount of ethyliodide is substituted for 2-chloroacetophenone, 2-[N-(β-ethylaminoethyl)-N-(2,5-dichlorophenyl)amino]acetophenone is obtained.

EXAMPLE 12

When in the procedure of Example 6 (A) appropriate amounts of an ω-haloalkyleneamine and formate derivative as listed below are substituted respectively for 1-amino-2-chloroethane and β,β,β-trichloroethyl chloroformate the respective protected amine derivative listed below is obtained:

| ω-Haloalkylene-amine | Formate derivative | Protected Amine |
|---|---|---|
| 1-amino-3-chloro-propane | benzyl chloroformate | benzyl N-(3-chloropropyl)carbamate |
| 1-amino-6-chloro-hexane | π-methoxybenzyl chloroformate | π-methoxybenzyl N-(6-chlorohexyl)-carbamate |
| 1-amino-4-chloro-butane | π-nitrobenzyl chloroformate | π-nitrobenzyl N-(4-chlorobutyl)-carbamate |
| 1-amino-5-chloro-pentane | tert-butyl azidoformate | π-tert-butyl N-(5-chloropentyl)-carbamate |

EXAMPLE 13

When in the procedure of Example 6 (B) appropriate amounts of benzyl N-(3-chloropropyl)carbamate and p-tert-butyl N-(5-chloropentyl)carbamate are reacted respectively with appropriate amounts of 2,5-dichloroaniline and p-trifluoromethylaniline, benzyl N-[γ-(2,5-dichloroaniline)propyl]carbamate and tert-butyl N-[ε-(4-trifluoromethylaniline)pentyl]carbamate are obtained respectively.

Upon reacting appropriate amounts of benzyl N-[γ-(2,5-dichloroaniline)propyl]carbamate and tert-butyl N-[ε-(4-trifluoromethylaniline)pentyl]carbamate respectively with appropriate amounts of 2-chloroacetophenone a 2',5'-dichloro-4-chlorobutyrophenone by the procedure of Example 5 the following respective products are obtained:

benzyl N-[γ-[N'-(2,5-dichlorophenyl)-N'-(benzoylmethyl)amino]propyl]carbamate and tert-butyl N-[ε-[N'-(4-trifluorophenyl)-N'-(benzoylpropyl)amino]pentyl]carbamate.

The benzyloxycarbonyl and tert-butoxycarbonyl protecting groups are removed from the above amine protected products by treating said products with trifluoroacetic acid at 0° C for 20 minutes followed by diluting the mixture with water and basifying with sodium hydroxide to pH 10 and extracting the final product with ether.

We claim:

1. A method of treating sickle cell anemia in a patient in need thereof which comprises administering to said patient in an amount effective to inhibit the sickling of red blood cells a compound of the formula

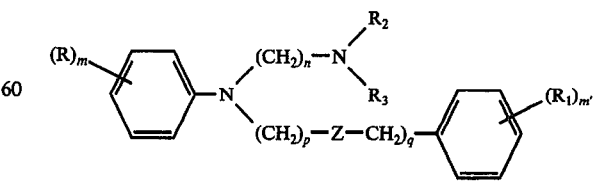

wherein each of R and $R_1$ is hydrogen, chlorine, fluorine, bromine, trifluoromethyl, hydroxy, a lower alkoxy group of from 1 to 4 carbon atoms or a straight or branched lower alkyl group of from 1 to 4 carbon atoms; $R_2$ is hydrogen or a straight or branched lower alkyl group of from 1 to 4 carbon atoms; $R_3$ is hydrogen or a straight or branched lower alkyl group of from 1 to 4 carbon atoms; Z is

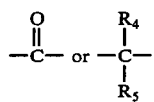

wherein $R_4$ is hydrogen or lower alkyl of from 1 to 4 carbon atoms, and $R_5$ is hydroxy or alkylcarbonyloxy wherein the alkyl moiety has from 1 to 4 carbon atoms; each of $m$ and $m'$ is the integer 1 or 2; $n$ is an integer of from 2 to 6; $p$ is an integer of from 1 to 3; and $q$ is an integer of from zero to 2; or pharmaceutically acceptable acid addition salts thereof.

2. A method of claim 1 wherein Z is

3. A method of claim 1 wherein Z is

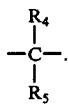

4. A method of claim 1 wherein each of $m$ and $m'$ is the integer 1.

5. A method of claim 1 wherein each of $m$ and $m'$ is the integer 2, and each of R and $R_1$ is selected from hydrogen, chlorine, fluorine, bromine, trifluoromethyl, hydroxy, a lower alkoxy group of from 1 to 4 carbon atoms and a straight or branched lower alkyl group of from 1 to 4 carbon atoms.

6. A method of claim 1 wherein each of $m$ and $m'$ is the integer 2 and each of R and $R_1$ is selected from chlorine, fluorine, bromine, hydroxy, a lower alkoxy group of from 1 to 4 carbon atoms and a straight chain alkyl group of from 1 to 4 carbon atoms.

7. A method of claim 1 wherein the compound is N-(β-diethylaminoethyl)-N-(β-hydroxy-β-phenethyl)-2,5-dichloroaniline or a pharmaceutically acceptable acid addition salt thereof.

8. A method of claim 1 wherein the compound is N-(β-diethylaminoethyl)-N-[β-hydroxy-β-(3,4-dichlorophenyl)ethyl]-2,5-dichloroaniline or a pharmaceutically acceptable acid addition salt thereof.

9. A method of claim 1 wherein the compound is N-(β-diethylaminoethyl)-N-(β-hydroxy-β-phenethyl)-4-chloroaniline or a pharmaceutically acceptable acid addition salt thereof.

10. A method of claim 1 wherein the compound is N-(β-diethylaminoethyl)-N-(β-hydroxy-β-phenethyl)-4-methoxyaniline or a pharmaceutically acceptable acid addition salt thereof.

11. A method of claim 1 wherein the compound is N-(γ-diethylaminopropyl)-N-(β-hydroxy-β-phenethyl)-2,5-dichloroaniline or a pharmaceutically acceptable acid addition salt thereof.

12. A method of claim 1 wherein the compound is N-(δ-diethylaminobutyl)-N-(β-hydroxy-β-phenethyl)-2,5-dichloroaniline or a pharmaceutically acceptable acid addition salt thereof.

13. A method of claim 1 wherein the compound is N-(β-aminoethyl)-N-(β-hydroxy-β-phenethyl)-2,5-dichloroaniline or a pharmaceutically acceptable acid addition salt thereof.

14. A method of claim 1 wherein the compound is N-(β-ethylaminoethyl)-N-(β-hydroxy-β-phenethyl)-2,5-dichloroaniline or a pharmaceutically acceptable acid addition salt thereof.

15. A method of claim 1 wherein the compound is 2-[N-(β-aminoethyl)-N-(2,5-dichlorophenyl)amino]-acetophenone or a pharmaceutically acceptable acid addition salt thereof.

16. A method of claim 1 wherein the compound is N-(β-diethylaminoethyl)-N-(β-hydroxy-β-phenylpropyl)-2,5-dichloroaniline or a pharmaceutically acceptable acid addition salt thereof.

17. A method of treating sickle cell anemia in a patient in need thereof which comprises administering to said patient in an amount effective to inhibit the sickling of red blood cells a compound of the formula

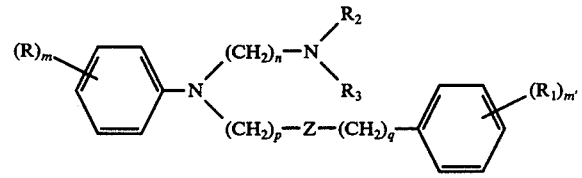

wherein each of R and $R_1$ is hydrogen, chlorine, fluorine, bromine, trifluoromethyl, hydroxy, a lower alkoxy group of from 1 to 4 carbon atoms or a straight or branched lower alkyl group of from 1 to 4 carbon atoms; $R_2$ is hydrogen or a straight or branched lower alkyl group of from 1 to 4 carbon atoms; $R_3$ is hydrogen or a straight or branched lower alkyl group of from 1 to 4 carbon atoms; Z is

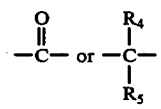

wherein $R_4$ is hydrogen or lower alkyl of from 1 to 4 carbon atoms, and $R_5$ is hydroxy; each of $m$ and $m'$ is the integer 1 or 2; $n$ is an integer of from 2 to 6; $p$ is an integer of from 1 to 3; and $q$ is an integer of from zero to 2; or pharmaceutically acceptable acid addition salts thereof.

* * * * *

UNITED STATES PATENT AND TRADEMARK OFFICE
CERTIFICATE OF CORRECTION

PATENT NO. : 4,060,630
DATED : Nov. 29, 1977
INVENTOR(S) : Dolfini et al.

It is certified that error appears in the above-identified patent and that said Letters Patent are hereby corrected as shown below:

Column 2, line 28 "represent methoxy" should read -- represent are methoxy --. Column 3, line 10, "That is, applicants'" should read -- That is, to applicants' --. Table I, 14th listing, 3rd Column, "(4-hydroxyphenylamino]" should read -- (4-hydroxyphenyl)amino] --. Column 13, line 15, 2nd Column "π-methoxyben-" should read -- $p$-methoxyben- --, line 15, 3rd Column "π-methoxybenzyl-" should read -- $p$-methoxybenzyl- --, line 17, 2nd Column "π-nitrobenzyl" should read -- $p$-nitrobenzyl --, line 17, 3rd Column "π-nitrobenzyl N-" should read -- $p$-nitrobenzyl N- --, line 19, 3rd Column, "π-tert-butyl N-" should read -- $p$-_tert_-butyl N- --.

Signed and Sealed this

Twelfth Day of September 1978

[SEAL]

Attest:

RUTH C. MASON
Attesting Officer

DONALD W. BANNER
Commissioner of Patents and Trademarks